United States Patent
Taylor et al.

(10) Patent No.: US 9,724,097 B2
(45) Date of Patent: *Aug. 8, 2017

(54) COIL FASTENER APPLIER WITH FLEXIBLE SHAFT

(71) Applicant: Covidien LP, Mansfield, MA (US)

(72) Inventors: Eric J. Taylor, East Hampton, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 14/682,673

(22) Filed: Apr. 9, 2015

(65) Prior Publication Data

US 2015/0209043 A1    Jul. 30, 2015

Related U.S. Application Data

(63) Continuation of application No. 11/544,477, filed on Oct. 6, 2006, now Pat. No. 9,017,345.

(51) Int. Cl.
*A61B 17/10*    (2006.01)
*A61B 17/068*    (2006.01)
(Continued)

(52) U.S. Cl.
CPC ........ *A61B 17/10* (2013.01); *A61B 17/00234* (2013.01); *A61B 17/068* (2013.01);
(Continued)

(58) Field of Classification Search
CPC ............ A61B 17/068; A61B 17/07207; A61B 2017/0649; A61B 17/00234
See application file for complete search history.

(56) References Cited

U.S. PATENT DOCUMENTS 5,258,000 A   11/1993   Gianturco
5,383,880 A    1/1995   Hooven
(Continued)

FOREIGN PATENT DOCUMENTS

WO    9811814 A2    3/1998
WO    03034895 A2    5/2003

OTHER PUBLICATIONS

European Search Report for EP 07253975.2-2310 date of completion is Feb. 13, 2008 (10 pages).

*Primary Examiner* — Gregory Anderson
*Assistant Examiner* — Christina Lauer

(57) ABSTRACT

A coil fastener applier including a housing, a flexible elongated tubular member, a flexible drive member, a fastener assembly and a trigger is disclosed. The housing defines a longitudinal axis and includes a stationary handle affixed thereto. The flexible elongated tubular portion extends distally from the housing. The flexible drive member is rotatably mounted within the flexible elongated tubular portion. The fastener assembly is mounted adjacent a distal portion of the flexible drive member and is configured to releasably mount at least one coil fastener thereon. The trigger is movably mounted on the housing and movement of the trigger rotates the flexible drive member to drive a coil fastener into tissue. The flexible elongated tubular member and the flexible drive member enable off-axis delivery of a coil fastener.

17 Claims, 19 Drawing Sheets

(51) Int. Cl.
*A61B 17/00* (2006.01)
*A61B 17/064* (2006.01)
*A61B 17/29* (2006.01)
*A61F 2/00* (2006.01)

(52) U.S. Cl.
CPC .............. *A61B 2017/00278* (2013.01); *A61B 2017/0645* (2013.01); *A61B 2017/0649* (2013.01); *A61B 2017/0688* (2013.01); *A61B 2017/2905* (2013.01); *A61B 2017/2925* (2013.01); *A61F 2002/0072* (2013.01)

(56) References Cited

U.S. PATENT DOCUMENTS

| | | |
|---|---|---|
| 5,433,721 A | 7/1995 | Hooven et al. |
| 5,439,156 A | 8/1995 | Grant et al. |
| 5,518,163 A | 5/1996 | Hooven |
| 5,518,164 A | 5/1996 | Hooven |
| 5,582,616 A | 12/1996 | Bolduc et al. |
| 5,667,517 A | 9/1997 | Hooven |
| 5,830,221 A | 11/1998 | Stein et al. |
| 5,897,562 A | 4/1999 | Bolanos et al. |
| 6,261,302 B1 | 7/2001 | Voegele et al. |
| 6,592,593 B1 * | 7/2003 | Parodi .................. A61B 17/064 606/108 |
| 6,743,239 B1 | 6/2004 | Kuehn et al. |
| 6,743,240 B2 | 6/2004 | Smith et al. |
| 6,824,548 B2 | 11/2004 | Smith et al. |
| 6,843,794 B2 | 1/2005 | Sixto, Jr. et al. |
| 6,945,979 B2 | 9/2005 | Kortenbach et al. |
| 7,070,602 B2 | 7/2006 | Smith et al. |
| 7,090,685 B2 | 8/2006 | Kortenbach et al. |
| 7,105,000 B2 | 9/2006 | McBrayer |
| 2002/0087169 A1 | 7/2002 | Brock et al. |
| 2004/0193186 A1 | 9/2004 | Kortenbach et al. |
| 2005/0049616 A1 | 3/2005 | Rivera et al. |
| 2005/0090837 A1 | 4/2005 | Sixto et al. |
| 2005/0090838 A1 | 4/2005 | Sixto et al. |
| 2005/0125010 A1 | 6/2005 | Smith et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2006/0100640 A1 | 5/2006 | Bolduc |
| 2006/0217742 A1 | 9/2006 | Messerly et al. |
| 2006/0217743 A1 | 9/2006 | Messerly et al. |

\* cited by examiner

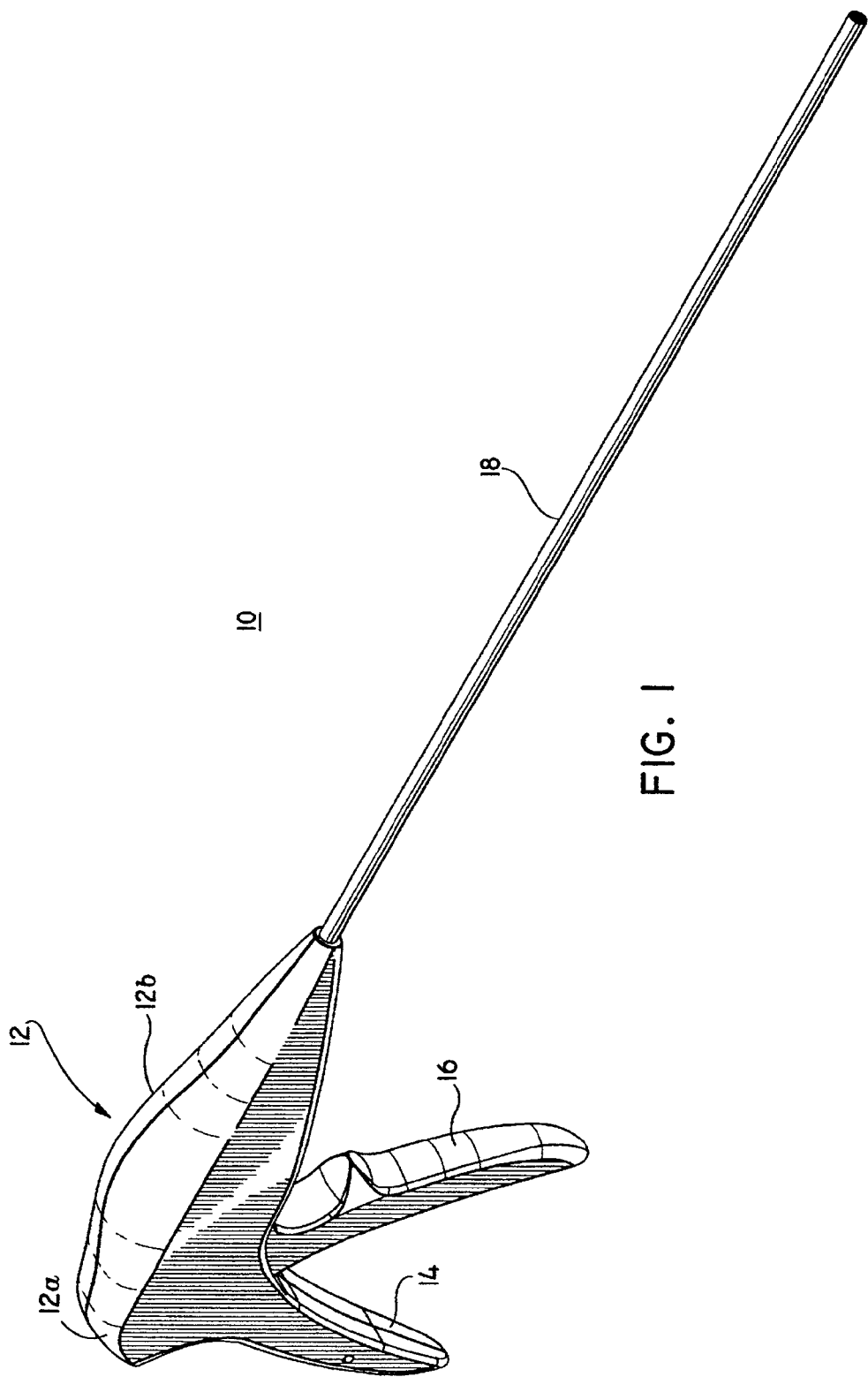

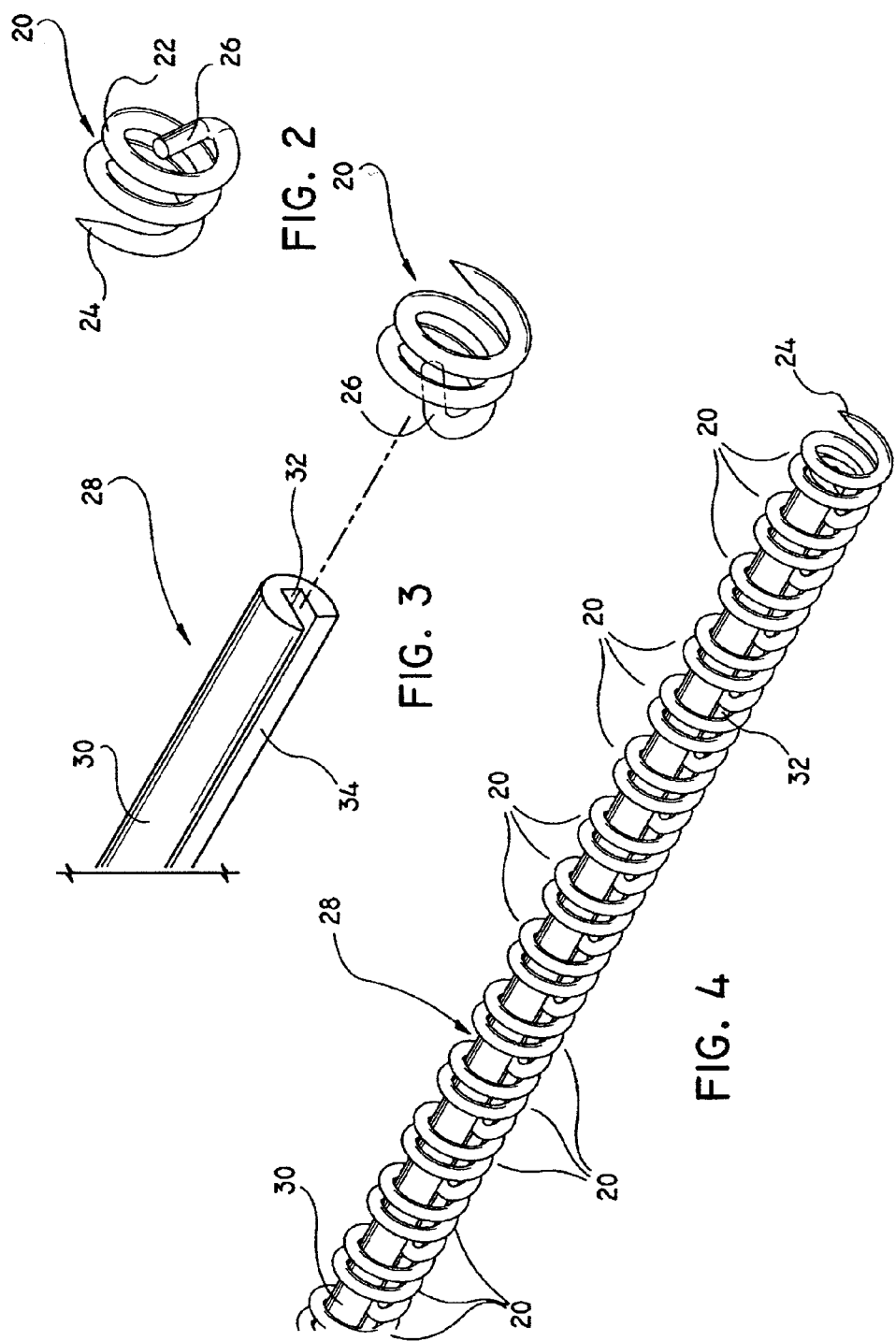

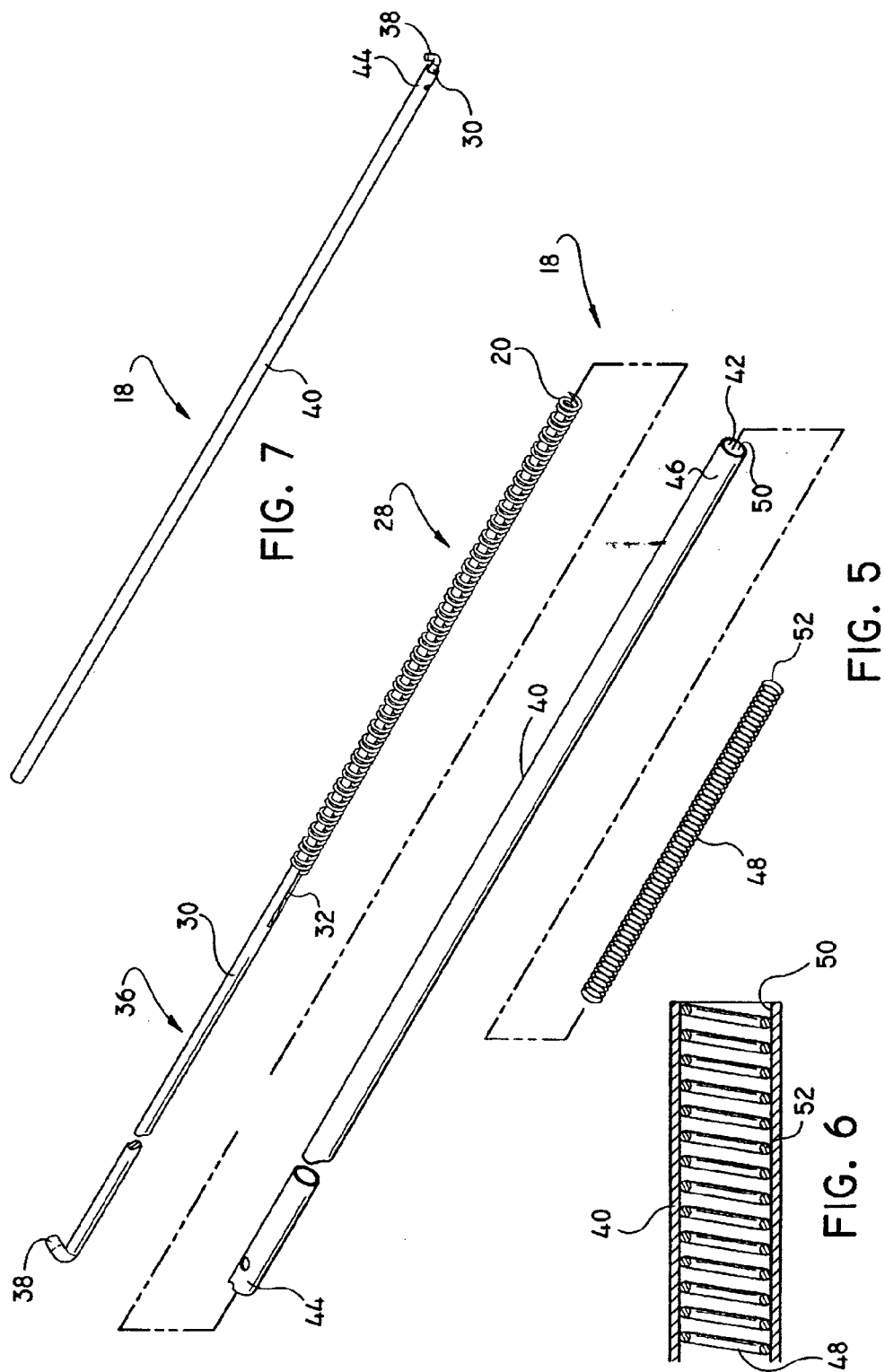

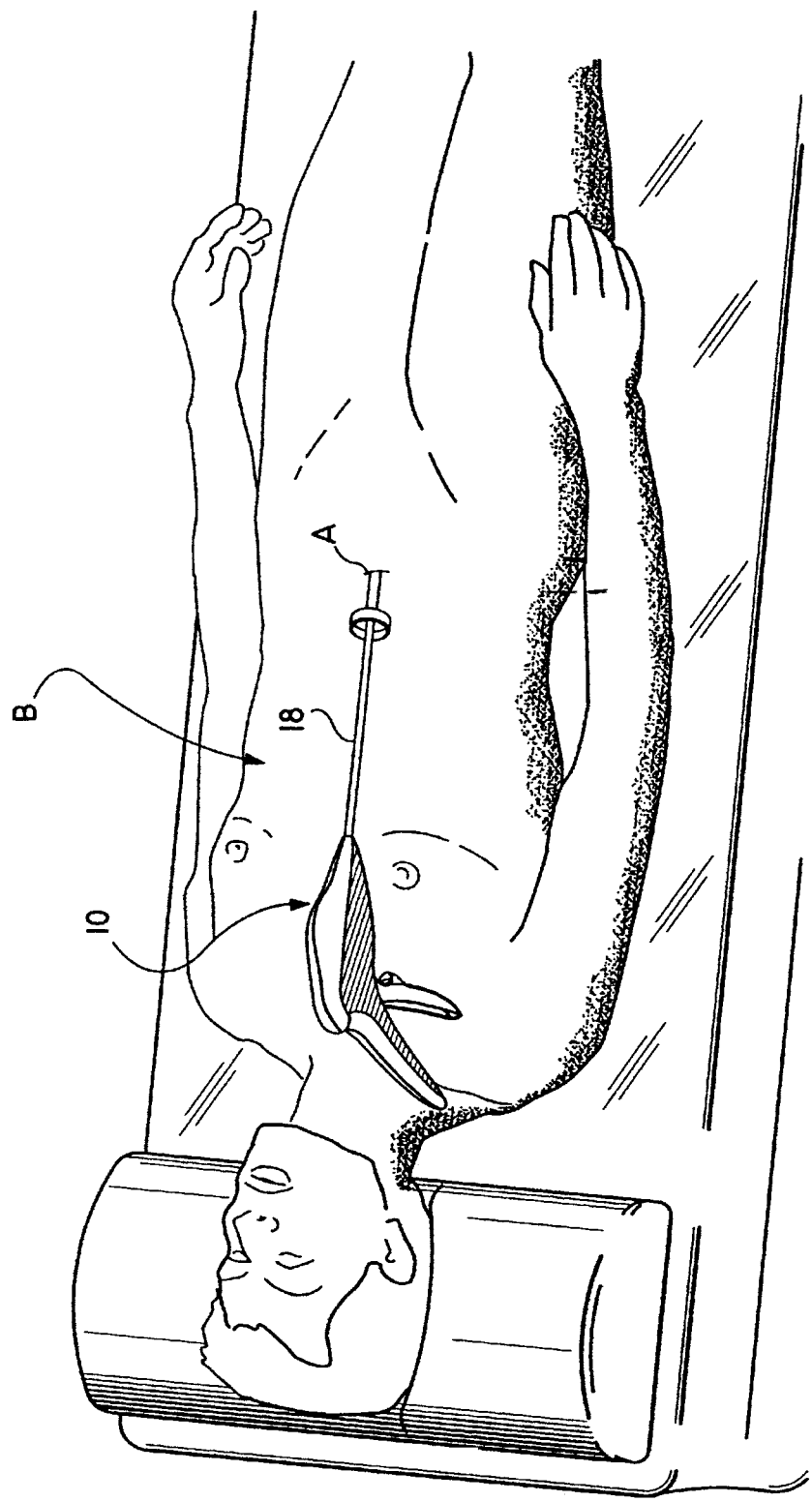

COIL FASTENER APPLIER WITH FLEXIBLE SHAFT

CROSS-REFERENCE TO RELATED APPLICATION

The present application is a continuation of U.S. patent application Ser. No. 11/544,477, filed on Oct. 6, 2006, the entire content of which being incorporated by reference herein.

BACKGROUND

Technical Field

The present disclosure relates to surgical apparatus for fastening objects to body tissue and, more particularly, to a coil fastener applier having a flexible shaft configured to apply helical coil fasteners to surgical mesh and tissue during surgical repair of the body tissue in procedures such as hernia repair.

Background of Related Art

Various surgical procedures require instruments capable of applying fasteners to tissue to form tissue connections or to secure objects to tissue. For example, during hernia repair it is often desirable to fasten a mesh to body tissue. In certain hernias, such as direct or indirect inguinal hernias, a part of the intestine protrudes through a defect in the support abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

Less invasive surgical procedures are currently available to repair a hernia. In laparoscopic procedures surgery is performed in the abdomen through a small incision while in endoscopic procedures, surgery is performed through narrow endoscopic tubes or cannulas inserted through small incisions in the body. Laparoscopic and endoscopic procedures generally require long and narrow instruments capable of reaching deep within the body and configured to seal with the incision or tube they are inserted through. Additionally, the instruments must be capable of being actuated remotely, that is, from outside the body.

Currently endoscopic techniques for hernia repair utilize fasteners, such as, surgical staples or clips, to secure the mesh to the tissue to provide reinforcement to the repair and structure for encouraging tissue ingrowth. The staples or clips need to be compressed against the tissue and mesh to secure the two together.

One other type of fastener suited for use in affixing mesh to tissue, during procedures such as hernia repair, is a coil fastener having a helically coiled body portion terminating in a tissue penetrating tip. An example of this type of fastener is disclosed in U.S. Pat. No. 5,258,000.

Existing coil fastener appliers are often designed for linear and non-intralumenal use, i.e., they are generally used for affixing mesh to an essentially flat tissue surface via a coil fastener. In certain situations, it may be desirable to fire surgical fasteners intralumenally. While some surgical instruments (e.g., surgical staplers) exist for firing surgical fasteners (e.g., surgical staples) in this manner, the prior art does not include a surgical instrument for firing a coil fastener within a tube-like organ, such as a colon or intestine, for example. Unlike the firing of surgical staples from a surgical stapler, for example, firing a coil fastener from a coil fastener applier generally requires rotational movement of the coil fastener. A coil fastener applier usable both intralumenally and non-intralumenally is desired.

SUMMARY

The present disclosure relates to a coil fastener applier including a housing, a flexible elongated tubular member, a flexible drive member, a fastener assembly and a trigger, where the flexible elongated tubular member and the flexible drive member enable off-axis delivery of a coil fastener. The housing defines a longitudinal axis and includes a stationary handle affixed thereto. The flexible elongated tubular portion extends distally from the housing. The flexible drive member is rotatably mounted within the flexible elongated tubular portion. The fastener assembly is mounted adjacent a distal portion of the flexible drive member and is configured to releasably mount at least one coil fastener thereon. The trigger is movably mounted on the housing and movement of the trigger rotates the flexible drive member to drive a coil fastener into tissue.

In an embodiment, the fastener assembly is substantially rigid and is configured to releasably mount between about three and about six coil fasteners thereon. In a disclosed embodiment, the length of the fastener assembly is between about 0.5 inches and about 1.5 inches. It is also disclosed that the fastener assembly includes at least one coil fastener thereon.

In an embodiment, the flexible elongated tubular portion includes a layer of braided steel and a plastic coating disposed about the layer of braided steel. In a disclosed embodiment, the flexible drive member is made essentially of flexible steel.

In a contemplated embodiment, the coil fastener includes an articulation mechanism. The articulation mechanism includes an articulation lever disposed on a portion of the housing and articulation cables. The articulation cables are each operably connected to the articulation lever adjacent their proximal ends and are operably connected to the fastener assembly adjacent their distal ends.

In an embodiment, the coil fastener includes a drive assembly disposed at least partially within the housing. It is disclosed that the drive assembly includes a plurality of gears, at least one of which being engagable with the flexible drive member for rotating the flexible drive member. It is also disclosed that the drive assembly includes an anti-reverse mechanism.

The present disclosure also relates to a method of applying coiled fasteners intralumenally. The method includes the steps of providing a coil fastener applier, as described above, providing at least one coil fastener on the fastener assembly, positioning the coil fastener adjacent an intralumenal tissue site and moving the trigger to cause a coil fastener to be ejected from the coil fastener applier.

DESCRIPTION OF THE DRAWINGS

An embodiment of the presently disclosed handle assembly incorporating an adjustable force-limiting mechanism is disclosed herein with reference to the drawings, wherein:

FIG. 1 is a perspective view of a coil fastener applier according to an embodiment of the present disclosure;

FIG. 2 is a perspective view of a helical coil fastener utilized with the coil fastener applier of FIG. 1;

FIG. 3 is a perspective view of a distal portion of a drive rod and a helical coil fastener;

FIG. 4 is a perspective view of the distal portion of the drive rod with a plurality of helical coil fasteners loaded thereon;

FIG. 5 is a perspective view, with parts separated, of an elongated tubular portion, a spring and the drive rod with a plurality of helical coil fasteners loaded on the distal portion thereof;

FIG. 6 is a sectional view of a distal portion of the elongated tubular portion with the spring installed therein;

FIG. 7 is a perspective view of the elongated tubular portion with the drive rod inserted therein;

FIG. 24 is a perspective view showing the use of the coil fastener applier in the patient;

DETAILED DESCRIPTION OF EMBODIMENTS

Figure 8:
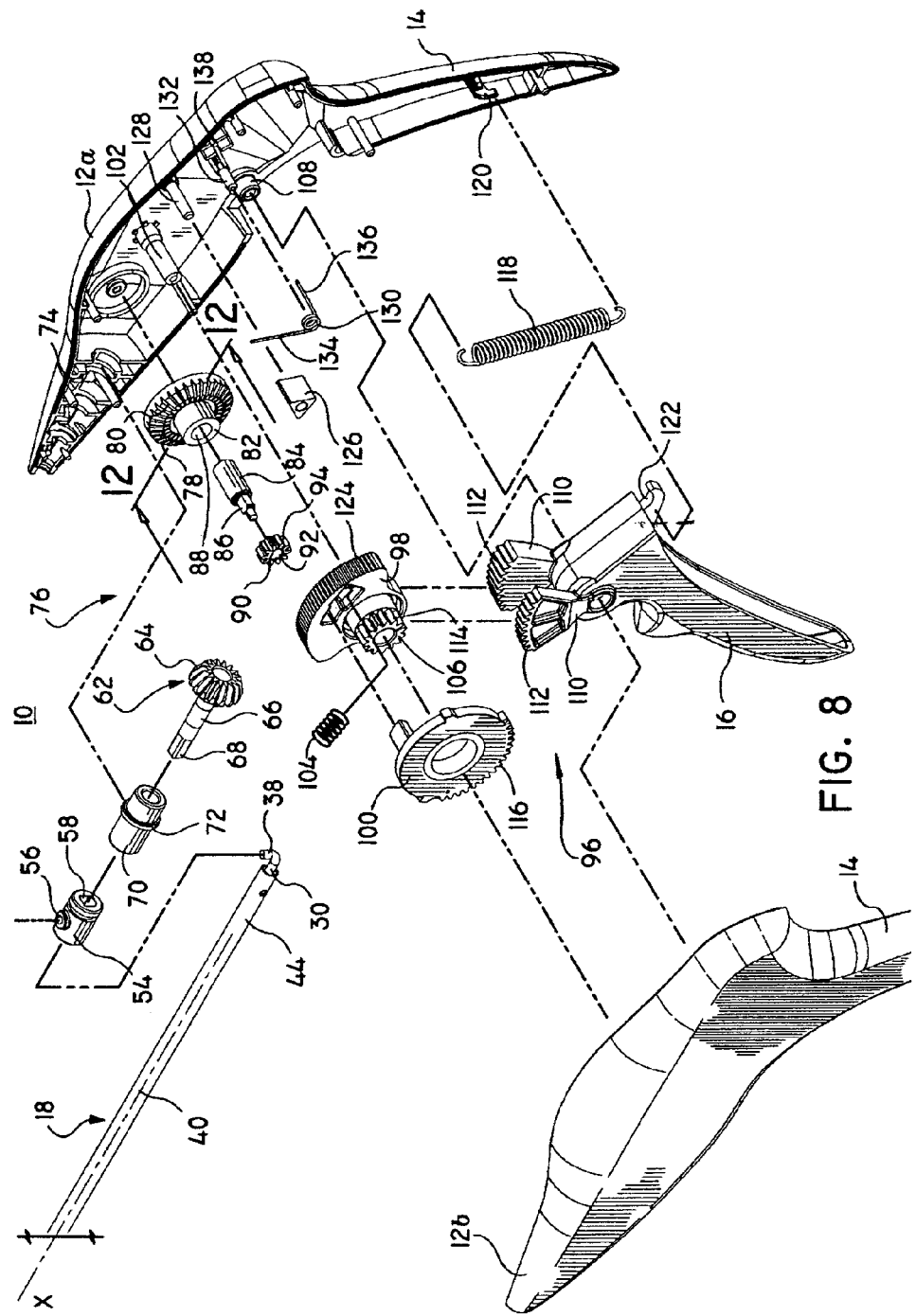
FIG. 8 is a perspective view, with parts separated, of a housing portion of the coil fastener applier of FIG. 1.

With reference now to the drawings wherein like numerals represent like elements throughout the several views and initially with respect to FIG. 1, there is disclosed an embodiment of a coil fastener applier 10. Coil fastener applier 10 is provided to apply helical-shaped coil fasteners to tissue or to secure mesh to tissue during surgical procedures such as hernia repair. Coil fastener applier 10 generally includes a housing 12 which may be formed as two separate housing halves 12a and 12b and a handle portion 14 extending from housing 12. A trigger 16 is movably mounted to housing 12. Trigger 16 is pivotally connected to housing 12 with a free end of trigger 16 spaced from a free end of handle portion 14. This arrangement provides an ergonomic advantage and positive secure control of trigger 16 and coil fastener applier 10. Coil fastener applier 10 also includes an elongated tubular portion 18 extending distally from housing 12. The elongated tubular portion 18 is provided to retain a plurality of coil fasteners for application to body tissue. In an embodiment, elongated tubular portion 18 is dimensioned to fit through conventional cannula structure. As used herein the term "distal" refers to that portion of the applier, or component thereof, farther from the user while the term "proximal" refers to that portion of the appliers or component thereof, closer to the user.

Referring now to FIG. 2, there is illustrated a helical-shaped coil fastener suitable for use with coil fastener applier 10. Coil fastener 20 is designed to be applied to tissue by rotating the coil into and through the tissue. Coil fastener 20 generally includes a coil body portion 22, illustrated having approximately 2½ coils and terminating in a sharp tissue penetrating point 24. A tang 26 is provided at an opposite end of coil body portion 22. Tang 26 extends generally inwardly toward the center of coil body portion 22 as shown. Coil fastener 20 may be formed of a suitable biocompatible material, such as, for example, stainless steel. However, coil fastener 20 may alternatively be formed of various elastomeric or polymeric materials and in addition may be formed of various bioabsorbable or biodegradable materials.

Referring now to FIG. 3, a distal portion 28 of a drive rod 30 associated with coil fastener applier 10 is provided to retain and drive coil fasteners 20. Distal portion 28 generally includes a longitudinally extending slot 32 extending along the length of distal portion 28. Slot 32 is provided to receive tang 26 therein such that upon rotation of drive rod 30 coil fastener 20 is similarly rotated. While slot 32 is illustrated as extending partially across drive rod 30, slot 32 may be formed completely through drive rod 30 to accommodate other types of coil or rotatable fasteners. A flat 34 extends adjacent slot 32 in distal portion 28.

As best shown in FIG. 4, a plurality of coil fasteners 20 may be arranged in a series longitudinally along the length of distal portion 28 of drive rod 30. Each coil fastener 20 has its associated tang 26 positioned within slot 32 of drive rod 30.

Referring now to FIG. 5, and as noted above, elongated tubular portion 18 contains a plurality of coil fasteners 20 and structure to drive coil fasteners 20 into tissue. A proximal portion 36 of drive rod 30 is of a generally solid circular cross-section such that slot 32 stops distally of proximal portion 36. A bent or L-shaped proximal end 38 of drive rod 30 is provided to assist in rotating drive rod 30 to advance coil fasteners 20 through elongated tubular portion 18 and drive coil fasteners 20 into tissue. Elongated tubular portion 18 also includes a generally tubular sleeve 40 defining a bore 42 therethrough and having a proximal end 44 and a distal end 46. Drive rod 30 is freely rotatable within bore 42 of tubular sleeve 40.

As best shown in FIGS. 5 and 6, in order to move successive coil fasteners 20 in a distal direction upon rotation of drive rod 30 there is provided a coiled spring 48 which may be braised or welded to an inner surface 50 of tubular sleeve 40. Coiled spring 48 creates a helical longitudinally extending surface 52 configured for engagement with the coil body portions 22 of coil fasteners 20. Thus, upon rotation of drive rod 30 coil fasteners 20 are moved along surface 52 and through tubular sleeve 40.

As best seen in FIG. 7, when assembled, L-shaped proximal end 38 of drive rod 30 extends out of proximal end 44 of tubular sleeve 40 for engagement with a drive assembly described hereinbelow.

Figure 9:
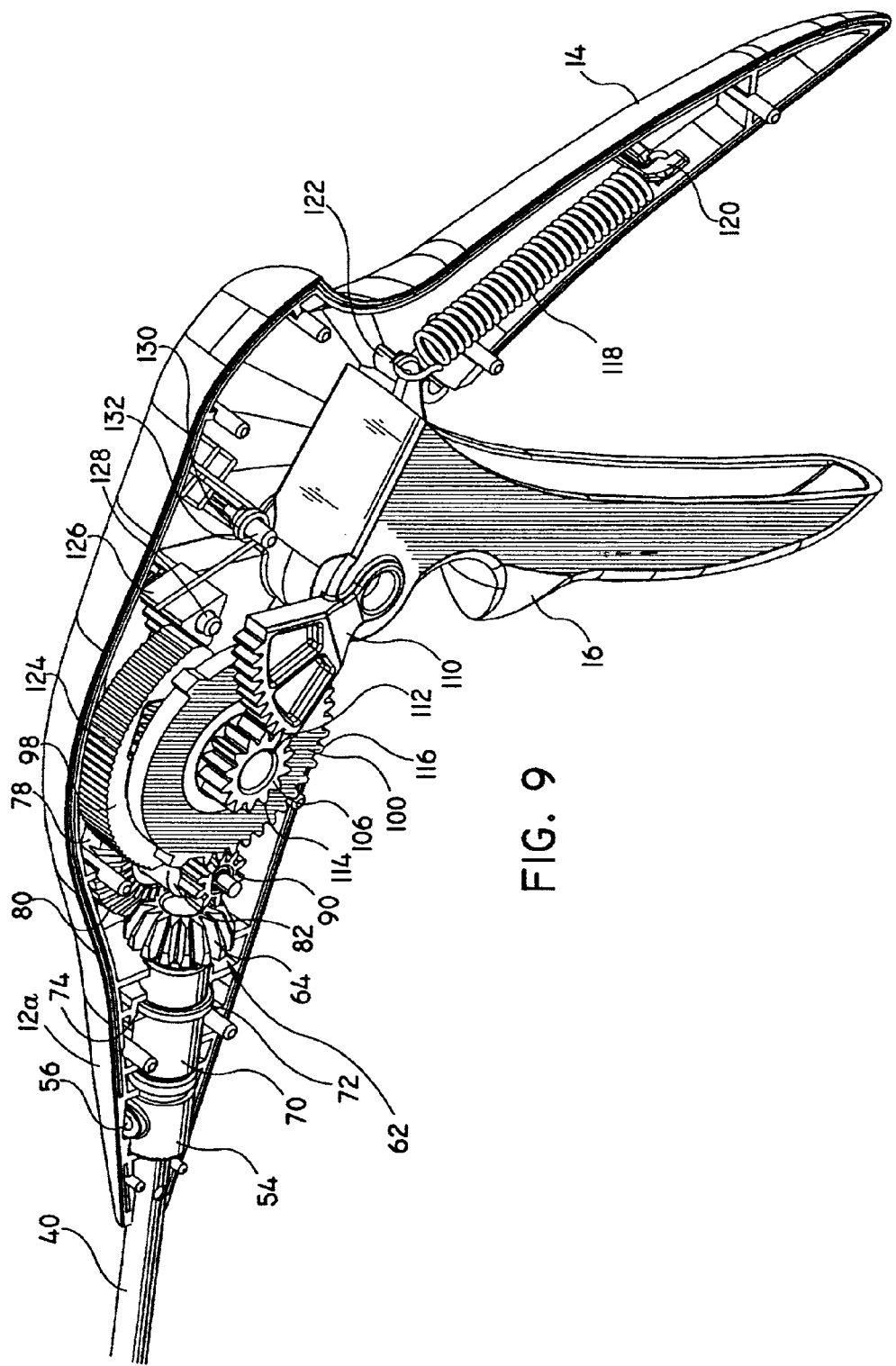
FIG. 9 is a perspective view of the housing portion of the coil fastener applier of FIG. 1 with the housing half removed.

Referring now to FIGS. 8 and 9, coil fastener applier 10 is provided with a hollow bearing 54 having a port 56 formed in one side thereof. Port 56 is provided to receive proximal end 38 of drive rod 30 in order to rotate drive rod 30 as bearing 54 is rotated. Hollow bearing 54 additionally includes a keyed opening 58 formed in a proximal face thereof. A first bevelled gear 62 is provided to rotate bearing 54 and generally includes a plurality of teeth 64 and a shaft 66 extending distally from teeth 64. First bevelled gear 62 includes a keyed distal end 68 which is configured to securely engage the keyed opening 58 in hollow bearing 54. Thus, upon rotation of first bevelled gear 62 drive rod 30 is rotated. As best seen in FIG. 8, first beveled gear 62 is oriented perpendicular to, and rotates about, a longitudinal axis x of elongated tubular portion 18. A hollow sleeve 70 is provided having a flange 72 which engages slots 74 in housing halves 12a and 12b. Sleeve 70 rotatably supports first bevelled gear 62 within housing 12.

First bevelled gear 62 forms a part of a drive assembly 76 provided to rotate drive rod 30 in a single direction. Drive assembly 76 additionally includes a second bevelled gear 78 having a plurality of teeth 80 configured to engage teeth 64 of first bevelled gear 62. As shown, first bevelled gear 62 is oriented perpendicularly to second bevelled gear 78. Thus, second bevelled gear 78 rotates in a plan parallel to longitudinal axis x. Second bevelled gear 78 is rotatably supported within housing 12 by means of a hub 82. A shaft 84 is secured within a bore 88 of hub 82. Shaft 84 includes a keyed end 86. A drive gear 90 is provided to rotate the drive assembly 76 and includes a keyed opening 92 for engagement with keyed end 86 of shaft 84. Drive gear 90 includes a plurality of teeth 94.

Coil fastener applier 10 additionally includes an actuation assembly 96 which, in combination with drive assembly 76, convert longitudinal motion of trigger 16 into rotary motion of drive rod 30. Actuation assembly 96 generally includes a ratchet-plate gear 98 and an idler gear 100, which are rotatably supported on a stud 102 formed in housing half 12a. A compression spring 104 is provided between ratchet-plate gear 98 and idler gear 100 in a manner described in more detail hereinbelow. A pair of trigger gears 106 are affixed to ratchet-plate gear 98 on either side thereof. It should be noted that trigger gears 106 as well as ratchet-plate gear 98, idler gear 100 and drive gear 90 all rotate in planes parallel to that of second bevelled gear 62 and thus of longitudinal axis x of elongated tubular portion 18.

As noted hereinabove, trigger 16 is movably mounted on housing 12. Trigger 16 is pivotably mounted about a stud 108 formed in housing halves 12a and 12b. Trigger 16 is provided with a pair of spaced apart gear portions 110 each having a plurality of teeth 112 which cooperate to engage and rotate teeth 114 on trigger gears 106. Thus, by pivoting trigger 16 about stud 108, gear portions 110 rotate trigger gears 106 and thus ratchet-plate gear 98 and idler gear 100. As shown, idler gear 100 includes a plurality of teeth 116 on an edge thereof. Teeth 116 are configured for engagement with drive gear 90 such that upon actuation of trigger 16 idler gear 110 is rotated to cause rotation of drive gear 90 and thus of drive rod 30. A return spring 118 is provided to bias trigger 16 into an initial position spaced apart from handle 14. Return spring 118 is affixed at one end to a stud 120 on housing half 12a and is affixed at an opposite end to a stud 122 on trigger 16.

Actuation assembly 96 additionally includes a ratchet and pawl mechanism which prevents return of trigger 16 to an initial position until trigger 16 has been fully depressed. Ratchet teeth 124 are shown formed along an edge of ratchet-plate gear 98. A pawl 126 is pivotally mounted about a stud 128 on housing half 12a and is engageable with ratchet teeth 124. Further, a biasing spring 130 is provided to bias pawl 126 into engagement with ratchet teeth 124. Biasing spring 130 is mounted about a stud 132 on housing half 12a and generally includes a first end 134 configured to engage pawl 126 and a second end 136 which is affixed within a slot 138 formed in housing 12a.

Figure 10:
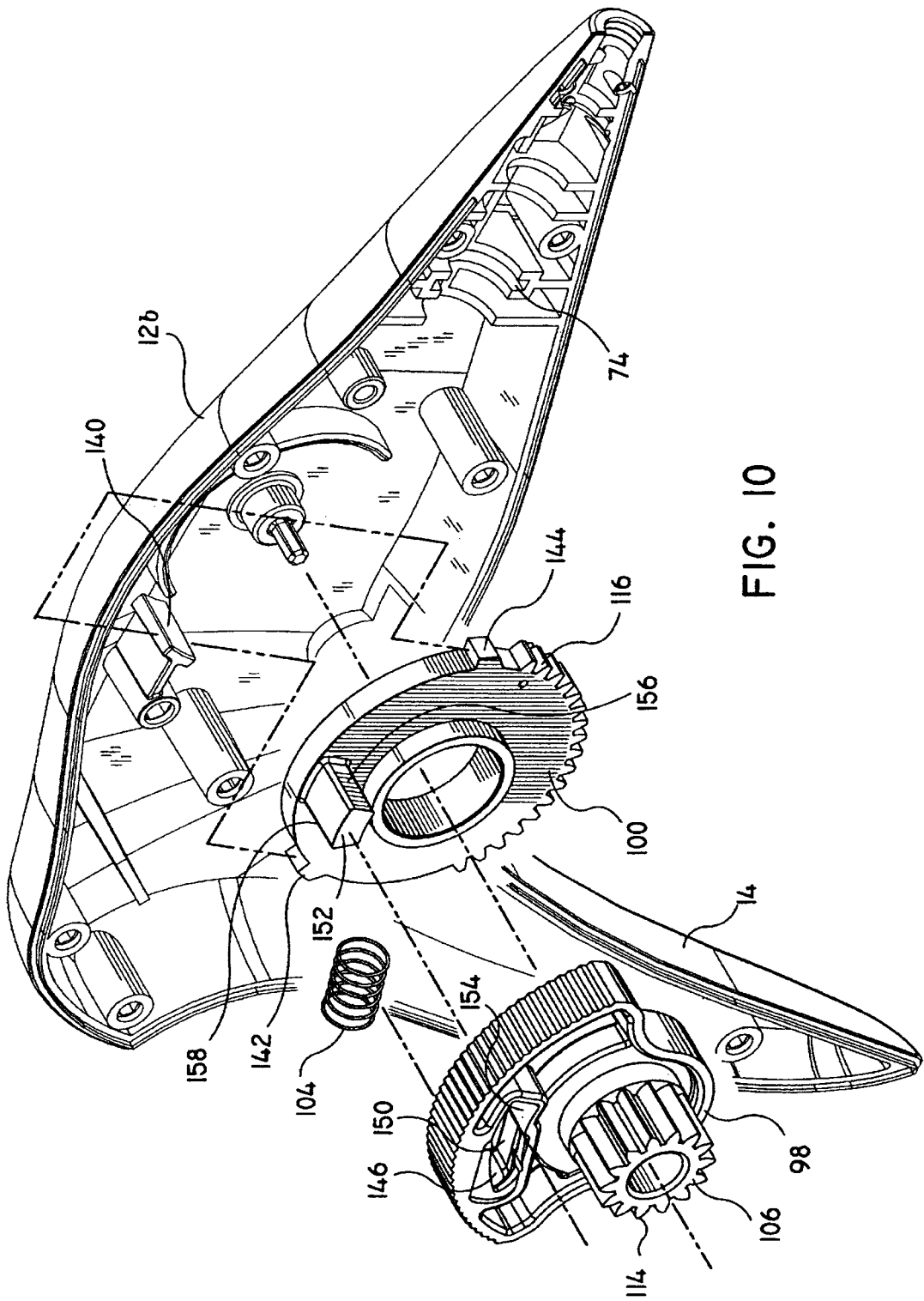
FIG. 10 is a perspective view of a housing half illustrating the positioning of the idler gear and the ratchet-plate gear.

Referring now to FIG. 10, structure is provided to prevent more than one coil fastener 20 from being driven out of coil fastener applier 10 upon a single pull of trigger 16. Housing half 12b includes a blocking member 140 fixedly mounted to housing half 12b. Blocking member 140 is configured to engage first and second stops 142 and 144, respectively, formed on idler gear 100. Second stop 144 limits the degree of rotation of idler gear 100 during actuation of coil fastener applier 10 to install a coil fastener 20 and first stop 142 limits the rotation of idler gear 100 upon release of trigger 16 enabling coil fastener applier 20 to return to an initial position ready to install another coil fastener 20. By providing first and second stops 142 and 144 and blocking member 140, the operator can be assured that drive rod 30 will be rotated a predetermined number of times and that only a single coil fastener 20 will be driven from coil fastener applier 10 at a single time.

Figure 11:
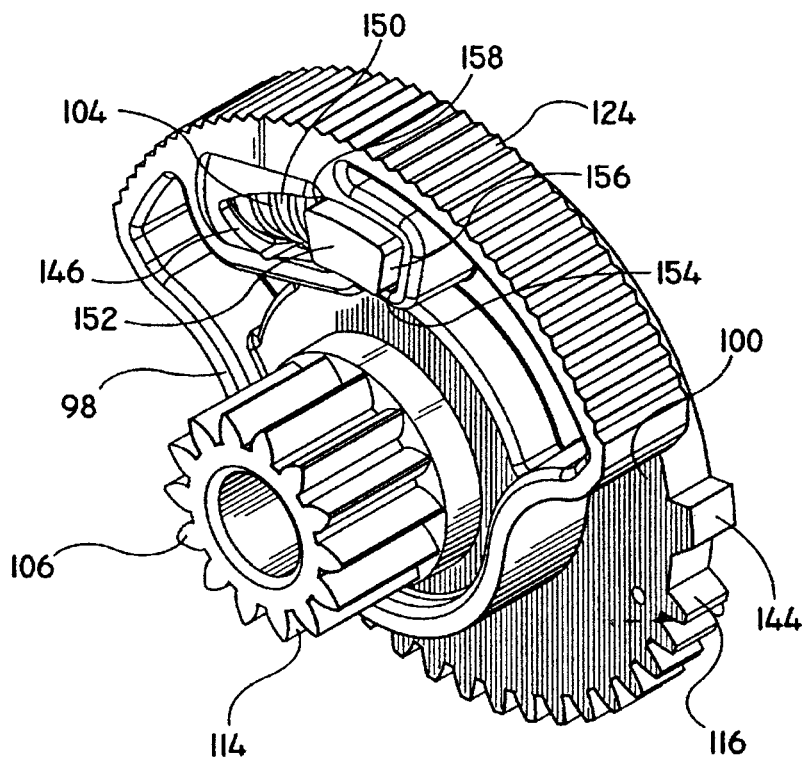
FIG. 11 is a perspective view of the assembled idler gear and ratchet-plate gear.

Turning now to FIGS. 10 and 11, ratchet-plate gear 98 is formed with a slot 146 which is configured to receive a compression spring 104 in a first portion 150 of slot 146. Compression spring 104 allows a slight amount of rotational movement to occur between ratchet-plate gear 98 and idler gear 100 during actuation and release of trigger 16 in a manner described in more detail hereinbelow. Idler gear 100 is formed with an engagement tab 152 projecting from a side thereof. Engagement tab 152 is positionable within a second portion 154 of slot 146. A first edge 156 of engagement tab 152 directly engages an edge 148 of ratchet-plate gear 98 while a second edge 158 of engagement tab 152 engages compression spring 104.

Figure 12:
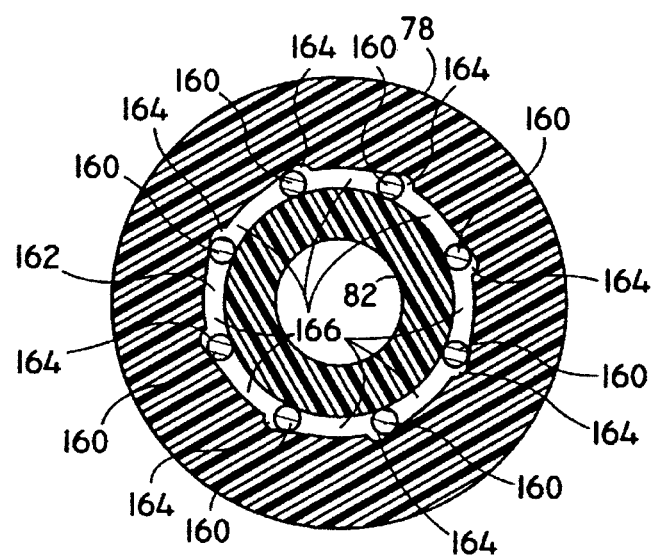
FIG. 12 is a sectional view taken along line 12-12 of FIG. 8 and illustrating a roller clutch mechanism.

Referring now to FIG. 12, coil fastener applier 10 includes an antireverse mechanism which provides for a free return of hub 82 independent of second bevelled gear 78. This allows hub 82 to rotate second bevelled gear 78 in a driving or first direction when hub 82 is rotated in the first direction to thereby drive coil fastener 20 from coil fastener applier 10. The anti-reverse mechanism disengages hub 82 from second bevelled gear 78 when hub 82 is rotated in a second direction. This is desirable so as to prevent rotation of drive rod 30 in a direction opposite that of its driving direction which would rotate coil fastener 20 such that coil fastener 20 is withdrawn from tissue or mesh or is further withdrawn within tubular portion 18. The anti-reverse mechanism is a roller clutch which is formed between hub 82 and second bevelled gear 78. A plurality of roller pins 160 are provided in a circumferential space or gap 162 defined between hub 82 and second bevelled gear 78. Gap 162 includes enlarged release areas 164 and reduced grasping areas 166. Thus, as hub 82 is rotated in a first direction to move roller pins 160 into the grasping areas 166, roller pins 160 are cammed within grasping areas 166 to form a solid connection between hub 82 and second bevelled gear 78. Alternatively, when hub 82 is rotated in the opposite or second direction, it moves roller pins 160 into enlarged release areas 164 allowing hub 82 to rotate freely and independently of second bevelled gear 78.

Figure 13:
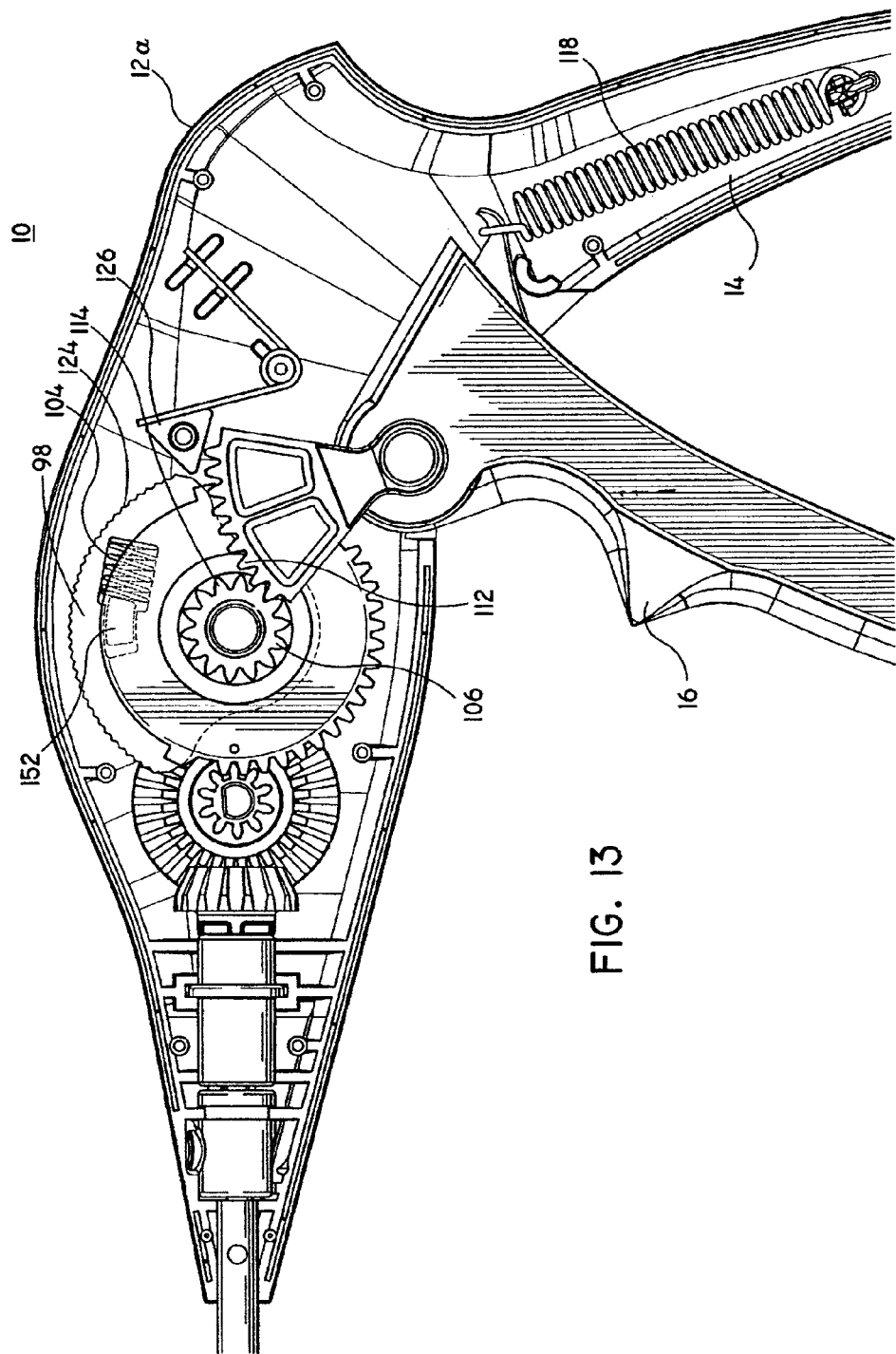
FIG. 13 is a side view, with a housing half removed, of the housing portion of the coil fastener applier in an initial position.
Figure 14:
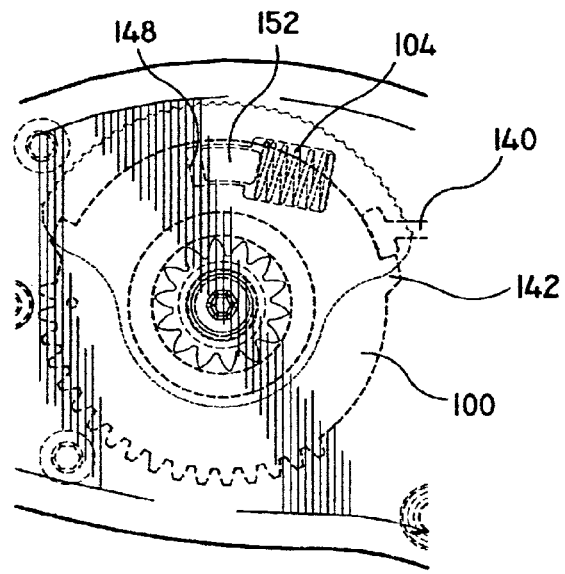
FIG. 14 is a partial side view, showing the positioning of the idler gear and ratchet-plate gear in an initial position corresponding to FIG. 13.

The operation of coil fastener applier 10 will now be described. Referring initially to FIG. 13, in an initial or starting position, trigger 16 is biased away from handle 14 due to the force of return spring 118. As shown, teeth 112 of trigger 16 are engaged with teeth 114 of trigger gears 106. Ratchet-plate gear 98 is in a counterclockwise most position, as viewed in FIG. 13, and pawl 126 is disengaged from teeth 124 of ratchet-plate gear 98. As best shown in FIG. 14, in the initial or starting position, blocking member 140 is engaged with first stop 142. In this position, with ratchet-plate gear in its counterclockwise most position and blocking member 140 engaged with first stop 142 of idler gear 100, engagement tab 152 is not engaged with edge 148 of ratchet-plate gear 98 but rather provides a slight compression to compression spring 104 as shown.

Figure 15:
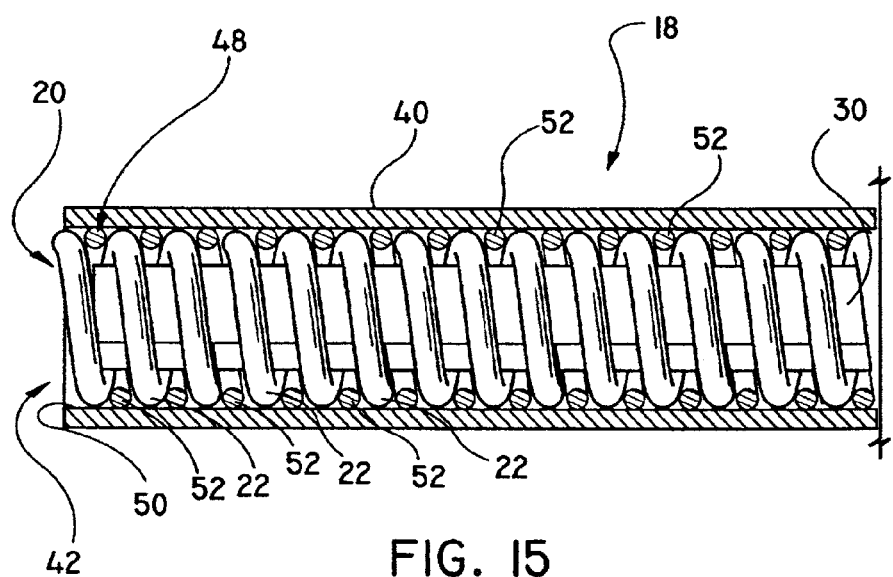
FIG. 15 is a perspective view, partially shown in cross-section, of a distal end portion of the coil fastener applier corresponding to FIG. 13.

Referring to FIG. 15, within distal end 46 of tubular sleeve 40, a plurality of coil fasteners 20 are slidably mounted about drive rod 30 and positioned within tubular sleeve 40. Each coil body portion 22 of each coil fastener 20 engages surface 52 of coil spring 48 which, as noted above, is firmly secured to inner surface 50 of tubular sleeve 40.

Figure 16:
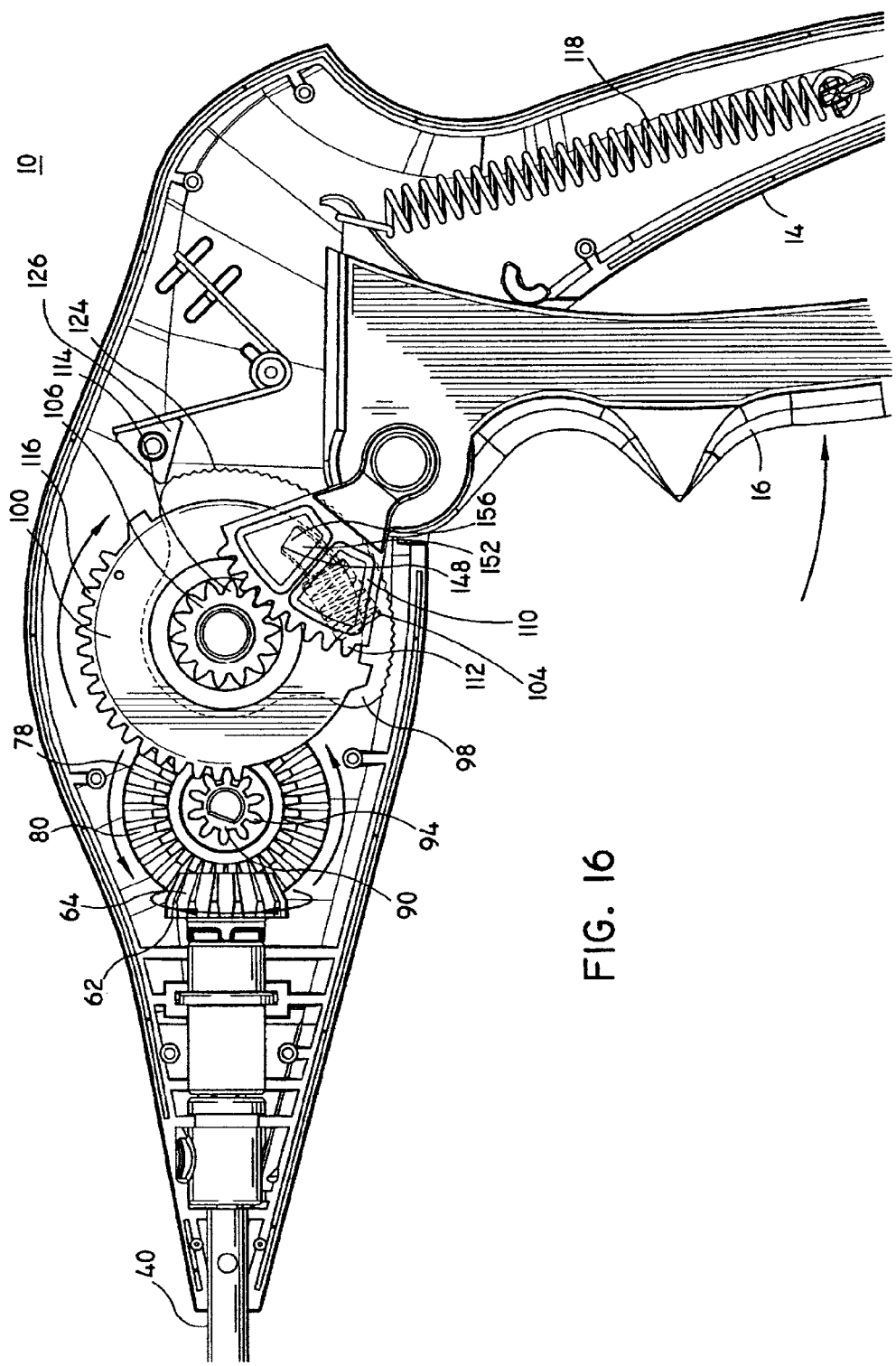
FIG. 16 is a view similar to FIG. 13 showing initial actuation of the coil fastener applier.
Figure 17:
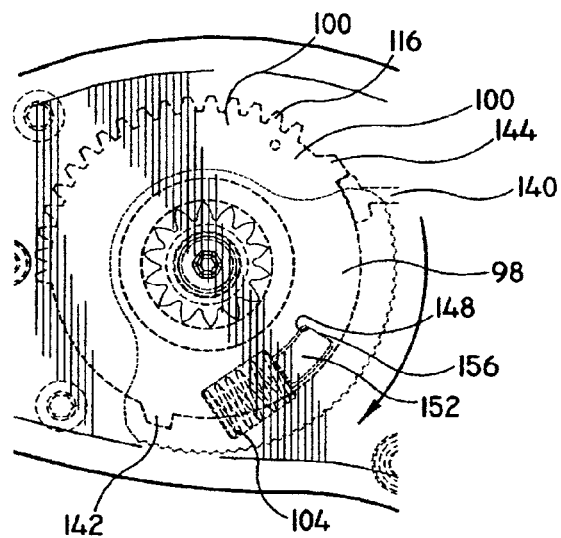
FIG. 17 is a view similar to FIG. 14 and corresponding to the position of FIG. 16.

Referring now to FIG. 16, to actuate coil fastener applier 10, trigger 16 is drawn toward handle 14 against the bias of return spring 118. As trigger 16 is moved, teeth 112 on gear portions 110 of trigger 16 engage and rotate teeth 114 of trigger gears 106 clockwise as seen in FIG. 16. As shown in FIGS. 16 and 17, rotation of trigger gears 106, rotates ratchet-plate gear 98 such that first edge 156 of engagement tab 152 engages ratchet-plate gear 98. Idler gear 100 thus rotates with ratchet-plate gear 98 allowing a short expansion of compression spring 104. As idler gear 100 is rotated in a clockwise direction, as viewed in FIG. 16, teeth 116 of idler gear 100 engaged and rotate drive gear teeth 94 of drive gear 90 counterclockwise.

Figure 18:
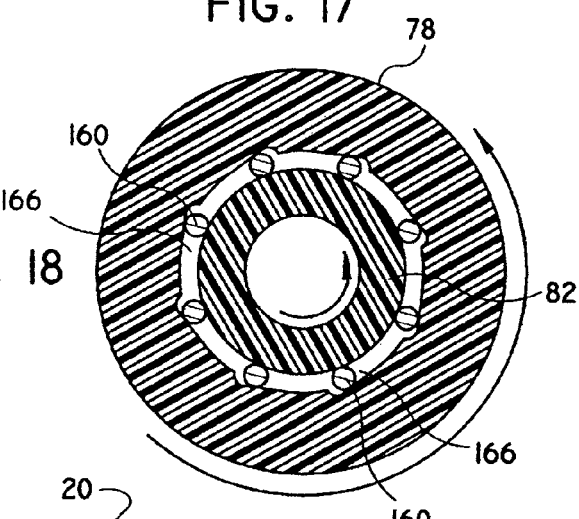
FIG. 18 is a sectional view of the roller clutch corresponding to FIG. 16.

Referring now for the moment to FIG. 18, as drive gear 90 and thus hub 82, are rotated in a counterclockwise direction, the rotation of hub 82 causes roller pins 160 to be forced into the reduced grasping areas 166 of gap 162. Once moved into grasping areas 166, roller pins 160 form a solid and secure connection between hub 82 and second bevelled gear 78. Thus, second bevelled gear 78 is rotated in a counterclockwise direction as shown in FIGS. 16 and 18. Referring now again to FIG. 16, upon rotation of second bevelled gear 78 in a counterclockwise direction, teeth 80 of second bevelled gear 78 engage teeth 64 of first bevelled gear 62 to thereby rotate drive rod 30 within tubular sleeve 40.

Figure 19:
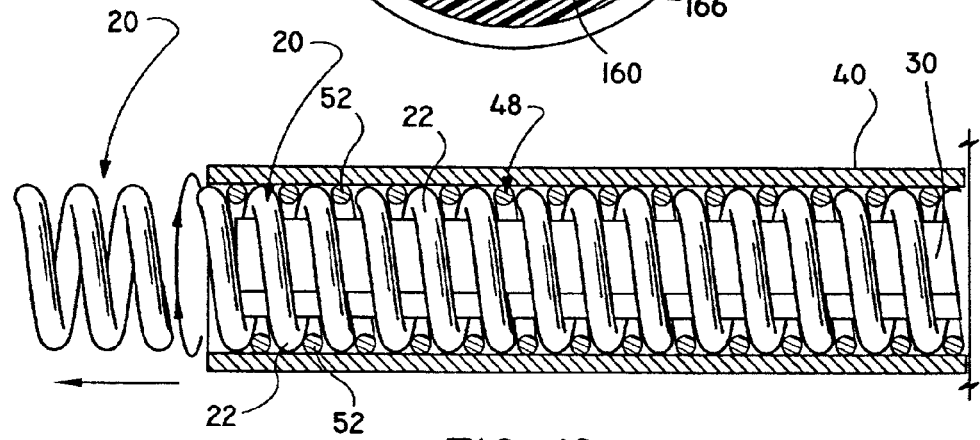
FIG. 19 is a perspective view, partially shown in cross-section, illustrating a helical coil fastener being driven out of the distal end of the coil fastener applier.

Referring now to FIG. 19, as drive rod 30 is rotated within tubular sleeve 40, drive rod 30 rotates coil fasteners 20. Coil fasteners 20, being engaged with surface 52 of coil spring 48, are moved distally within tubular sleeve 40 by engagement of coil body portions 22 with surface 52. Thus, rotation of drive rod 30 rotates or screws a coil fastener out of the distal end of elongated tubular portion 18. As shown, this rotation of drive rod 30 also moves a next successive coil fastener 20 into position to be applied to tissue during a next cycling of coil fastener applier 10.

Referring back to FIG. 16, it should be noted that upon a complete depression of trigger 16, drive rod 30 is rotated precisely a predetermined amount such that only one coil fastener 20 is driven out of the distal end of elongated tubular portion 18. During compression of trigger 16, pawl 126 engages and rides over teeth 124 of ratchet-plate gear 98. Should handle 16 be stopped during depression at any intermediate position, pawl 126 is engaged with teeth 124 to ensure that ratchet-plate gear 98 and idler gear 100 are not rotated in an opposite direction thereby preventing only partial insertion or withdrawal of coil fastener 20, i.e. preventing a partial drive cycle. As shown in FIG. 16, upon complete depression of trigger 16, pawl 126 passes over teeth 124 and is disengaged therefrom.

Referring to FIG. 17, upon a complete depression of trigger 16, idler gear 100 rotates between a position wherein first stop 142 is rotated away from blocking member 140 until a position where blocking member 140 engages second stop 144 to thereby prevent further rotation of idler gear 100. This degree of rotation of idler gear 100 corresponds exactly to the amount of rotation of drive rod 30 necessary to completely drive a single coil fastener 20 out of elongated tubular portion 18 and into tissue.

Figure 20:
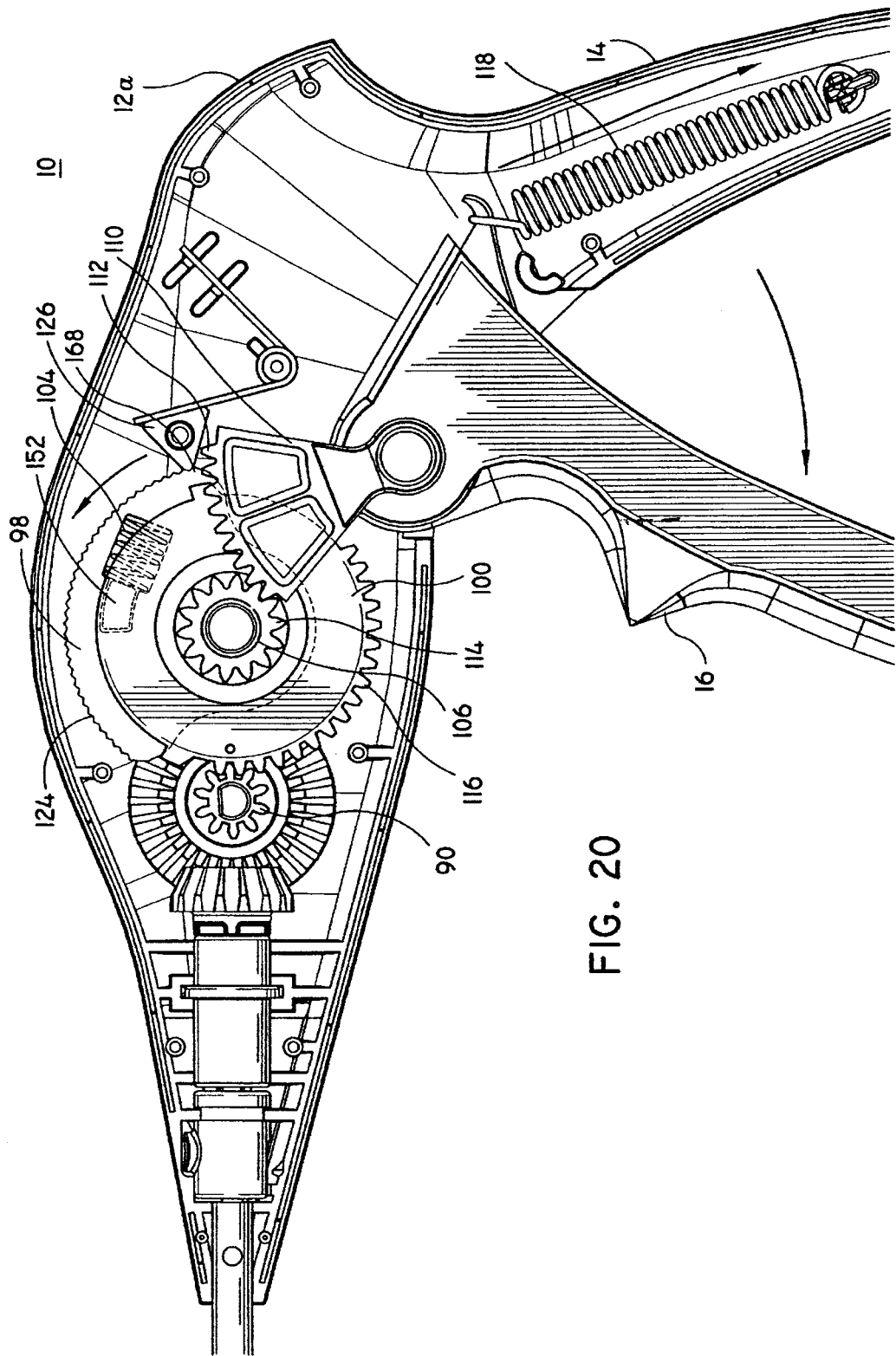
FIG. 20 is a side view of the housing portion, with a housing half removed, illustrating initial release of a trigger and positioning of the idler gear and the ratchet-plate gear.

Referring now to FIG. 20, once trigger 16 had been completely depressed and a coil fastener 20 has been driven from elongated tubular portion 18 into tissue mesh or other suitable structure, trigger 16 may be released. Trigger 16 is then biased to an open or initial position due to the force of return spring 118. As trigger 16 is moved to an open position, teeth 112 of gear portions 110 rotate teeth 114 of trigger gears 106 counterclockwise, as viewed in FIG. 20, and thus ratchet-plate gear 98 in a counterclockwise direction. As ratchet-plate gear 98 is rotated in a counterclockwise direction, compression spring 104 forces idler gear 100 also in a counterclockwise direction. With idler gear 100 rotating in a counterclockwise direction, teeth 116 of idler gear 100 rotate drive gear 90 in a clockwise direction.

Figure 21:
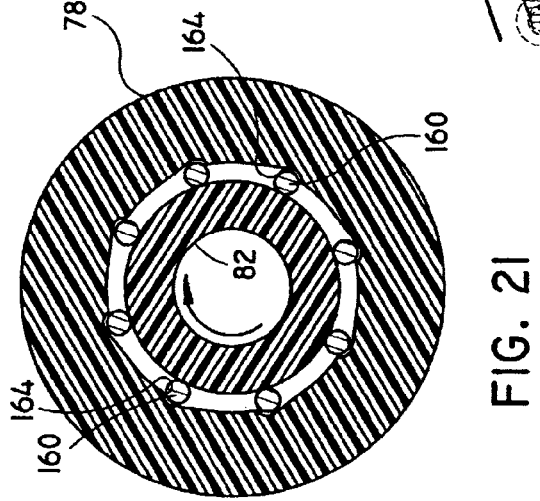
FIG. 21 is a sectional view of the roller clutch corresponding to FIG. 20.

Referring now for the moment to FIG. 21, as noted hereinabove, coil fastener applier 10 includes an anti-reverse mechanism or roller clutch which disengages drive rod 30 from rotation upon release of trigger 16 and allows a free return of drive gear 90 to a start position. Thus, upon clockwise rotation of hub 82, hub 82 moves roller pins 160 into the enlarged release areas 164. Since clutch pins 160 no longer form a solid firm contact between hub 82 and second bevelled gear 78, hub 82 is free to rotate independently of second bevelled gear 78 thereby preventing any rotation of drive rod 30.

Figure 23:
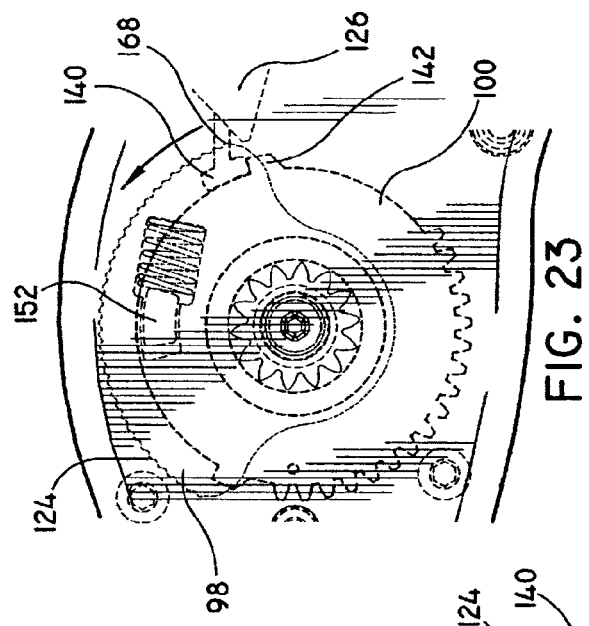
FIG. 23 is a view similar to FIG. 22 after complete release of the trigger.
Figure 22:
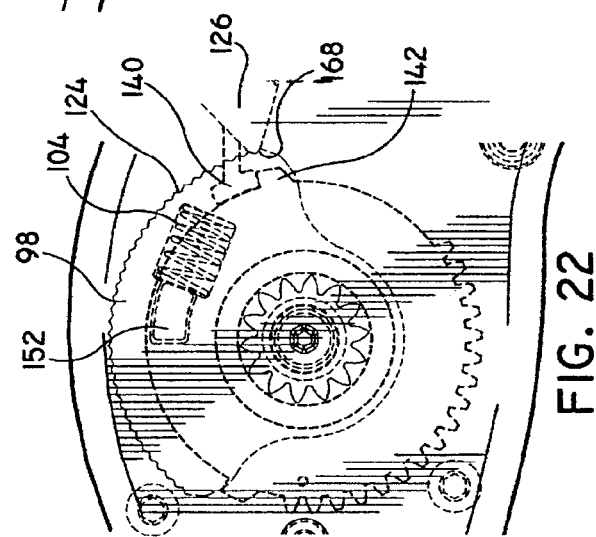
FIG. 22 is a partial side view showing the positioning of the idler gear and ratchet-plate gear along with a pawl corresponding to the position of FIG. 20.

Referring to FIGS. 20 and 22 and 23, during release of trigger 16, pawl 126 moves along teeth 124 of ratchet-plate gear 98 until pawl 126 rests on a last tooth 168. This corresponds with the engagement of blocking member 140 with first stop 142 to thereby prevent any further rotation of idler gear 100. Once pawl 126 has reached its position on last tooth 168, the tension of return spring 118, being greater than the force of compression spring 104, forces trigger 16 a little further allowing trigger gears 106 to move ratchet-plate gear 98 slightly against the force of compression spring 104. As best shown in FIG. 23, the force of return spring 118 overcomes the force of compression spring 104 forcing engagement tab 152 to compress return spring 104. This compression of return spring 118 allows ratchet-plate gear 98 to move slightly enabling pawl 126 to move off of last tooth 168 of ratchet-plate gear 98. Thus, coil fastener apparatus 10 is returned to initial position ready to be actuated again and install another coil fastener.

Referring now to FIG. 24, coil fastener applier 10 is shown positioned through a small incision A made in a patient B for use in a surgical procedure, such as, for example, hernia repair.

Figure 25:
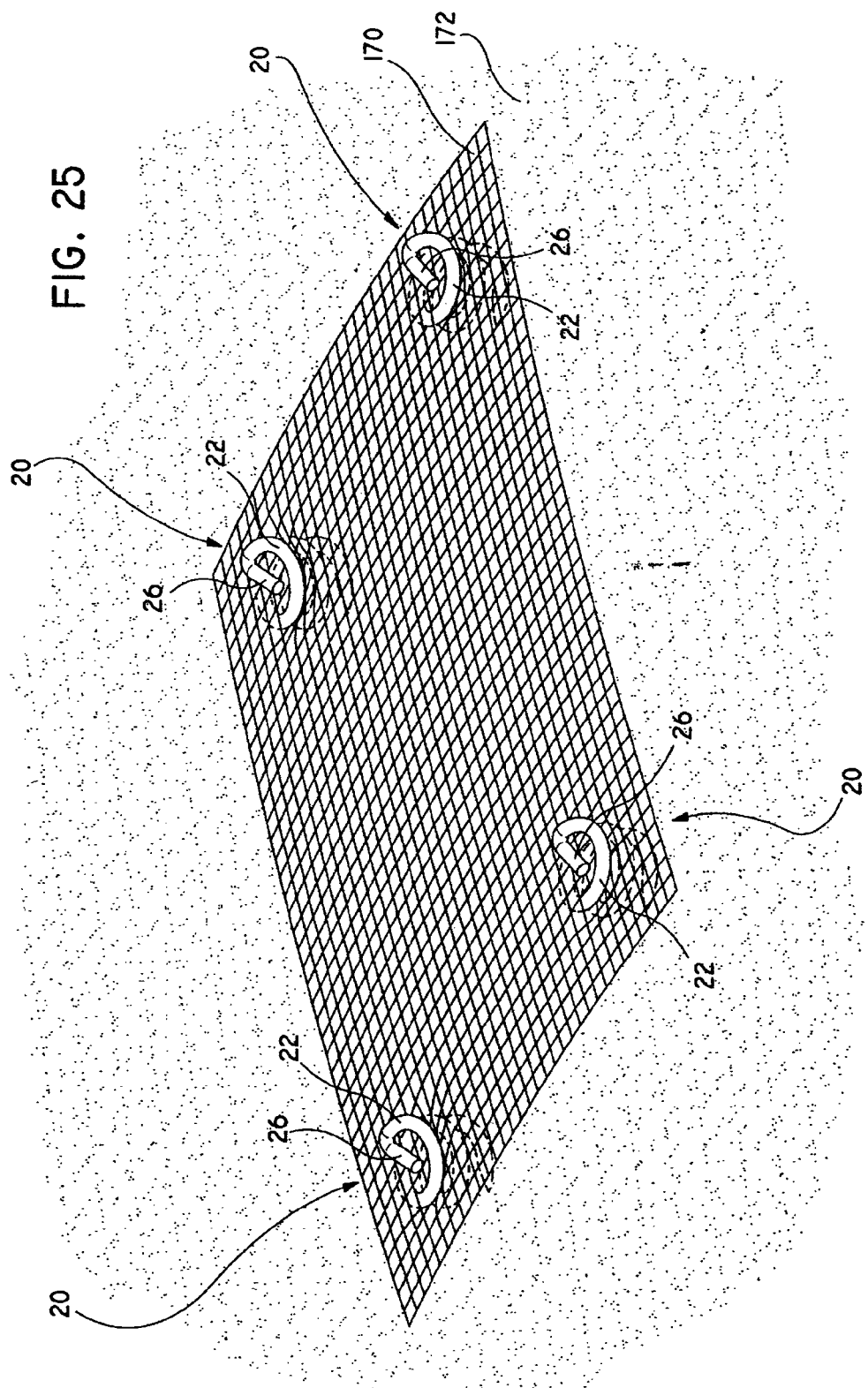
FIG. 25 is a perspective view of a tissue section and a surgical mesh secured to the tissue section by a plurality of helical coil fasteners.

Referring now to FIG. 25, when used for hernia repair, surgical coil fastener applier 10 may be utilized to affix a portion of a suture mesh 170 to a tissue section 172. As shown in FIG. 25, several coil fasteners 20 may be utilized to secure mesh 170 to tissue 172. It is disclosed that, in applying coil fasteners 20, coil fasteners 20 are rotated through mesh 170 and tissue 172 such that only approximately 180 degrees of coil body portion 22 along with tang 26 extend externally of the mesh 170. Tang 26 provides an anchoring or securing mechanism to prevent mesh 170 from sliding off of coil body portion 22 of coil fastener 20.

Figure 27:
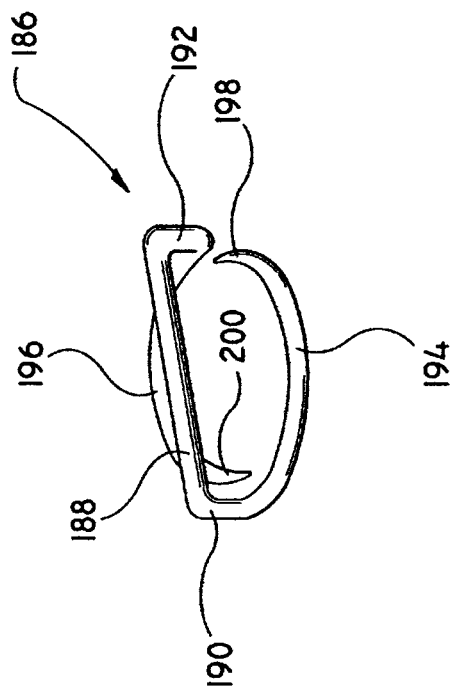
FIG. 27 is a perspective view of another alternate coil fastener.
Figure 26:
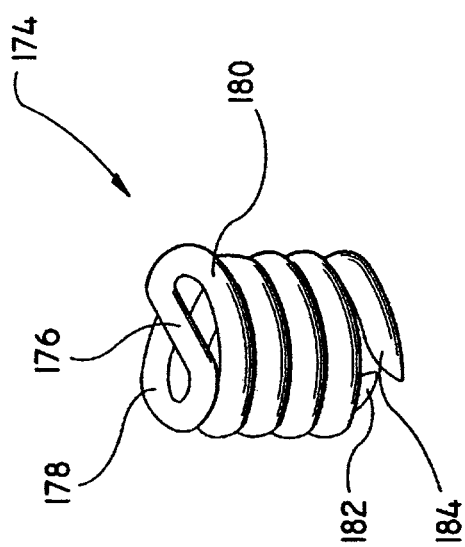
FIG. 26 is a perspective view of an alternate coil fastener.

Referring now to FIGS. 26 and 27, there are disclosed alternate embodiments of coil fasteners suitable for use with coil fastener applier 10. Referring first to FIG. 26, an alternate embodiment coil fastener 174 is formed with a straight backspan 176 and helical coil body portions 178, 180 extending from each end of back span 176. Tissue penetrating points 182, 184 is provided at a free end of respective body portions 178, 180. Backspan 176 engages a slot extending completely through a drive rod (not shown) and is slidably supported thereon. Rotation of the drive rod rotates coil fastener 174 within sleeve 40 of coil fastener applier 10 and into tissue.

Referring now to FIG. 27, in a further alternative embodiment, a coil fastener 186 is formed with a straight backspan 188 having straight legs 190, 192 extending from each end of backspan 188 and which are parallel to each other. Semi-circular tissue penetrating portions 194, 196 terminating in tissue penetrating points 198, 200 extend from a free end of respective leg 190, 192. Semi-circular tissue penetrating portions 194, 196 are located in a common plane which is generally parallel to backspan 188. The backspan of the coil fastener also engages a completely slotted drive rod (not shown) and is rotated thereby.

Referring now to FIGS. 28-31, a coil fastener applier 310 having a flexible elongated tubular portion 320 is shown. Coil fastener applier 310 includes a housing 312, a flexible elongated tubular portion 320, a flexible drive member 330, a fastener assembly 340 and a trigger 316. Housing 312 defines a longitudinal axis A-A (FIG. 28) and includes a stationary handle 315 affixed thereto. Flexible elongated tubular portion 320 extends distally from housing 312. Flexible drive member 330 is rotatably mounted within flexible elongated tubular portion 320. Fastener assembly 340 is mounted adjacent a distal portion 332 (FIG. 29) of flexible drive member 330. Fastener assembly 340 is configured to releasably mount at least one coil fastener 174 (FIG. 29) thereon. Trigger 316 is movably mounted on housing 312 and movement of trigger 316 rotates flexible drive member 330 to drive coil fastener 174 into tissue (e.g., a colon or intestine), not explicitly shown in this embodiment. Flexible elongated tubular portion 320 and flexible drive member 330 enable off-axis (i.e., not along or parallel to axis A-A) delivery of a coil fastener 174. That is, coil fastener 174 may be delivered in any reasonable direction intersecting axis A-A at an angle ∀ (including all reasonable angles with respect to the x-, y- and z-axes), such as in the direction illustrated by arrow B in FIG. 28.

Figure 29:
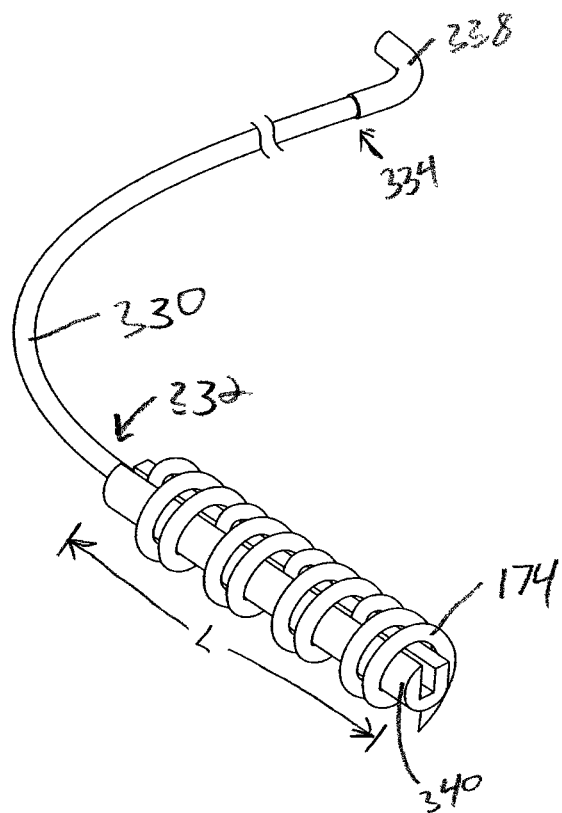
FIG. 29 is a perspective view of a flexible drive member and a fastener assembly of the coil fastener of FIG. 28, illustrated with coil fasteners on the fastener assembly.

Referring to FIG. 29, the illustrated embodiment of flexible drive member 330 includes a bent or L-shaped member 338 at its proximal end 334 and is mounted to fastener assembly 340 at its distal end. It is envisioned that flexible drive member 330 is connected to L-shaped member 338 and to fastener assembly 340 via braising. L-shaped member 338 mechanical cooperates with a drive assembly 76 (see FIG. 8) to facilitate rotation of flexible drive member 330, as described above with respect to drive rod 30.

Figure 28:
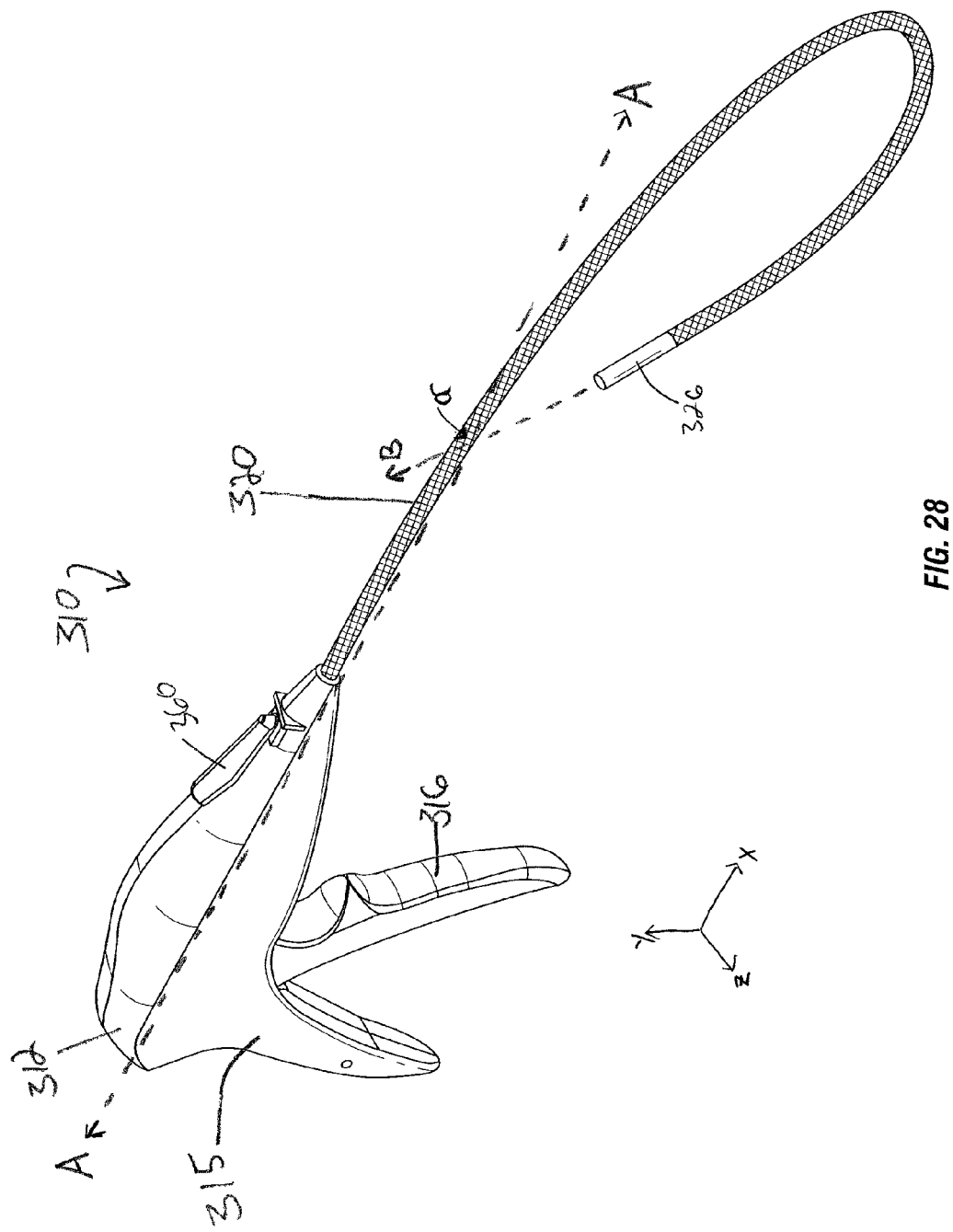
FIG. 28 is a perspective view of a coil fastener applier having a flexible shaft, in accordance with an embodiment of the present disclosure.

Fastener assembly 340 is illustrated in FIG. 29 as a substantially rigid member that is configured to releasably mount at least one coil fastener 174. In FIG. 28, fastener assembly is hidden from view behind a distal portion 326 of flexible elongated tubular portion 320. In the embodiment shown in FIG. 29, four coil fasters 174 are illustrated mounted on fastener assembly 340. It is envisioned that any reasonable number of coil fasteners 174 are mounted or mountable to fastener assembly 340, including between about three and about six coil fasteners 174. As shown in FIG. 28, the length of fastener assembly 340 in relation to the total length of flexible elongated tubular portion 320 is relatively short. The rigidity of fastener assembly 340 allows coil fasteners 176 to be mounted thereon and fired therefrom, but its short length enables a majority of the length of coil fastener applier 310 (i.e., flexible elongated tubular portion 320) to follows a curvilinear path of a tubular organ. In an embodiment, the length L of fastener assembly 340 is between about 0.5 inches and about 1.5 inches and is more particularly between about 0.75 inches and about 1.0 inches.

Figure 30:
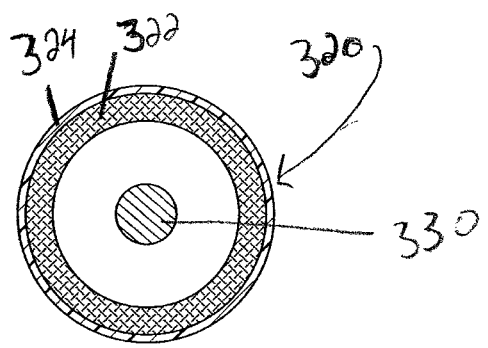
FIG. 30 is a cross-sectional view of a tubular sleeve and the flexible drive member of the coil fastener of FIGS. 28 and 29.

Referring to FIG. 30, a cross-section of flexible elongated tubular portion 320 and flexible drive member 330 is shown. Flexible elongated tubular portion 320 includes a first layer 322 and a second layer 324. In an embodiment, first layer 322 includes a braided steel material that enables flexible elongated tubular portion 320 to flex along its length. It is disclosed that second layer 324 includes a plastic coating surrounding first layer 322. Such a plastic coating may protect first layer 322, facilitate motion through a body part, and enables flexible elongated tubular portion 320 to maintain its flexibility. Flexible elongated tubular member 330 is illustrated about flexible drive member 330. Flexible drive member 330 or cable is made of a material that enables its flexibility and is substantially rigid enough to be rotated along its (possibly) curved length. One material that flexible drive member 330 may be made from is flexible steel.

The flexible qualities of flexible elongated tubular member 320 and flexible drive member 300 facilitate the guiding of fastener assembly 340 within a body lumen. In an embodiment, at least distal portion 326 of flexible elongated tubular portion 320 is inserted into a lumen (not explicitly shown in this embodiment). Housing 312 is then pushed distally to advance flexible elongated tubular portion 320 through the lumen. Flexible elongated tubular portion 320 is able to be guided and/or steered through the lumen by having the ability to flex/bend along its length to at least somewhat conform to any convolutions of the lumen. Flexible elongated tubular portion 320 (and flexible drive member 330) are rigid enough to advance through material/fluid within a lumen and are also flexible enough to curve/bend when a portion of flexible elongated tubular portion 320, e.g., distal portion 326, contacts an internal wall of the lumen.

Figure 31:
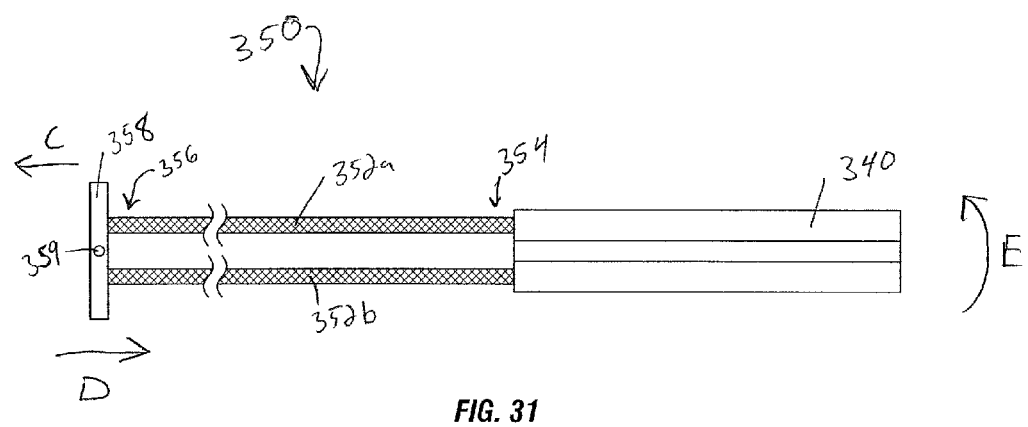
FIG. 31 is a plan view of an articulation assembly of the coil fastener of FIGS. 28-31.

Referring to FIG. 31, an articulation mechanism 350 is illustrated. Articulation mechanism 350 may facilitate the intralumenal positioning of a portion of coil fastener applier 310, e.g., fastener assembly 340. In the illustrated embodiment, articulation mechanism 350 includes a pair of articulation cables 352a, 352b and an articulation lever 360 (or other suitable structure) pivotally mounted on housing 312 (FIG. 28). Articulation cables 352a, 352b are each operably connected (e.g., braised) to fastener assembly 340 adjacent their distal ends 354. Each articulation cable 352a, 352b is operably connected to articulation lever 360, e.g., via an articulation link 358, adjacent their proximal ends 356. Pivotal movement of articulation lever 360 causes articulation cables 352a, 352b to move in opposite directions and thus causes fastener assembly 340 to articulate relative to housing 312. For example, movement of articulation lever 360 may cause articulation link 358 to move about pivot 359 in the direction of arrow C, thus pulling articulation cable 352a proximally. This movement also pushes articulation cable 352b distally in the direction of arrow D and causes fastener assembly 340 to articulate in the general direction of arrow E.

Articulation cables 352a, 352b are illustrated being operably connected to a proximal portion of fastener assembly 340 and within flexible elongated tubular portion 320 (not shown in FIG. 31). In another embodiment of the present disclosure, articulation cables 352a, 352b may extend along an outer perimeter of flexible elongated tubular portion 320 (e.g., between first layer 322 and second layer 324 or external of second layer 324) and may be operably connected adjacent distal portion 326 of flexible elongated tubular portion 320 (not explicitly shown in this embodiment).

The present disclosure also relates to a method of applying coiled fasteners 174 intralumenally. The method includes providing coil fastener applier 310, as described above, providing at least one coil fastener 174 on fastener assembly 340, positioning coil fastener applier 310 adjacent an intralumenal tissue site and moving trigger 316 to cause coil fastener 174 to be ejected from coil fastener applier 310.

It will be understood that various modifications may be made to the embodiments disclosed herein. For example, a shorter elongated tubular portion containing more or less coil fasteners may be provided for greater ease of handling during open surgery. Various articulations may be provided along the length of the elongated tubular portion to facilitate positioning of the coil fastener applier within the body. Additionally various configurations of the drive rod and slots or fastener retaining structure may be provided to accommodate various types of rotary fasteners. Therefore, the above description should not be construed as limiting, but merely as exemplifications of various embodiments. Those skilled in the art will envision other modifications within the scope and spirit of the claims appended hereto.

The invention claimed is:

1. A coil fastener applier, comprising:
   a housing;
   a flexible elongated tubular portion extending distally from the housing;
   a flexible drive member rotatably mounted at least partially within the flexible elongated tubular portion; and
   a fastener assembly connected to a distal portion of the flexible drive member, the fastener assembly configured to releasably mount at least one coil fastener thereon,
   wherein the flexible elongated tubular portion and the flexible drive member enable off-axis delivery of at least one coil fastener.

2. The coil fastener applier of claim 1, wherein the fastener assembly is substantially rigid.

3. The coil fastener applier of claim 1, wherein the fastener assembly is configured to releasably mount between about three and about six coil fasteners thereon.

4. The coil fastener applier of claim 1, wherein a length of the fastener assembly is between about 0.5 inches and about 1.5 inches.

5. The coil fastener applier of claim 1, wherein the flexible elongated tubular portion includes a layer of braided steel.

6. The coil fastener applier of claim 5, wherein the flexible elongated tubular portion includes a plastic coating disposed about the layer of braided steel.

7. The coil fastener applier of claim 1, wherein the flexible drive member is made essentially of flexible steel.

8. The coil fastener applier of claim 1, further including an articulation mechanism including an articulation lever and articulation cables, the articulation lever disposed on a portion of the housing, the articulation cables operably connected to the articulation lever adjacent their proximal ends and operably connected to the fastener assembly adjacent their distal ends.

9. The coil fastener applier of claim 1, further including a drive assembly disposed at least partially within the housing.

10. The coil fastener applier of claim 9, wherein the drive assembly includes gears, at least one of the gears engagable with the flexible drive member for rotating the flexible drive member.

11. The coil fastener applier of claim 9, wherein the drive assembly includes an anti-reverse mechanism.

12. The coil fastener applier of claim 1, wherein the fastener assembly includes at least one coil fastener mounted thereon.

13. A method of applying a coil fastener, comprising:
   providing a coil fastener applier, including:
      a housing defining a first axis;
      a flexible elongated tubular portion extending distally from the housing;
      a flexible drive member rotatably mounted at least partially within the flexible elongated tubular portion; and
      a fastener assembly connected to a distal portion of the flexible drive member, the fastener assembly configured to releasably mount at least one coil fastener thereon;
   positioning at least one coil fastener on the fastener assembly; and
   delivering the at least one coil fastener along a second axis, the second axis offset from the first axis.

14. The method of claim 13, wherein positioning at least one coil fastener on the fastener assembly includes positioning between about three and about six coil fasteners on the fastener assembly.

15. The method of claim 13, further comprising articulating the fastener assembly with respect to the housing.

16. The method of claim 13, further comprising rotating the fastener assembly with respect to the housing.

17. The method of claim 13, wherein delivering the at least one coil fastener along the second axis includes the first axis defining an acute angle with respect to the second axis.

* * * * *